United States Patent [19]

Grainger et al.

[11] Patent Number: 5,599,844
[45] Date of Patent: *Feb. 4, 1997

[54] PREVENTION AND TREATMENT OF PATHOLOGIES ASSOCIATED WITH ABNORMALLY PROLIFERATIVE SMOOTH MUSCLE CELLS

[75] Inventors: David J. Grainger; James C. Metcalfe; Peter L. Weissberg, all of Cambridge, United Kingdom

[73] Assignee: NeoRx Corporation, Seattle, Wash.

[ * ] Notice: The term of this patent shall not extend beyond the expiration date of Pat. No. 5,472,985.

[21] Appl. No.: 528,810

[22] Filed: Sep. 15, 1995

Related U.S. Application Data

[63] Continuation of Ser. No. 300,357, Sep. 2, 1994, Pat. No. 5,472,985, which is a continuation of Ser. No. 61,714, May 13, 1993, abandoned.

[51] Int. Cl.⁶ .................................................. A61K 31/135
[52] U.S. Cl. ........................................ 514/651; 514/824
[58] Field of Search .......................... 514/56, 651, 824

[56] References Cited

U.S. PATENT DOCUMENTS

| | | | |
|---|---|---|---|
| 4,235,988 | 11/1980 | Fildes et al. | 528/79 |
| 4,442,119 | 4/1984 | Magarian et al. | 424/274 |
| 4,824,436 | 4/1989 | Wolinsky | 604/53 |
| 4,826,672 | 5/1989 | Milius et al. | 424/1 |
| 4,839,155 | 6/1989 | McCague | 424/1 |
| 4,859,585 | 8/1989 | Sonnenschein et al. | 435/29 |
| 4,879,315 | 11/1989 | Magarian et al. | 514/754 |
| 4,973,755 | 11/1990 | Grafe et al. | 564/324 |
| 4,990,538 | 2/1991 | Harris et al. | 514/648 |
| 4,997,652 | 3/1991 | Wong | 424/428 |
| 5,015,666 | 5/1991 | Magarian et al. | 514/754 |
| 5,032,679 | 7/1991 | Brandley et al. | 536/21 |
| 5,047,431 | 9/1991 | Schickaneder et al. | 514/648 |
| 5,049,132 | 9/1991 | Shaffer et al. | 604/101 |
| 5,098,903 | 3/1992 | Magarian et al. | 514/255 |
| 5,112,305 | 5/1992 | Barath et al. | 704/96 |
| 5,120,535 | 6/1992 | Marquardt et al. | 424/85.5 |
| 5,140,012 | 8/1992 | McGovern et al. | 514/19 |
| 5,166,143 | 11/1992 | Ondetti et al. | 514/89 |
| 5,171,217 | 12/1992 | March et al. | 604/53 |
| 5,189,046 | 2/1993 | Burch et al. | 514/330 |
| 5,192,525 | 3/1993 | Yang et al. | 424/1.1 |
| 5,208,019 | 5/1993 | Hannson et al. | 424/85 |
| 5,216,024 | 6/1993 | Markaverich et al. | 514/543 |
| 5,219,548 | 6/1993 | Yang et al. | 424/1.1 |
| 5,221,620 | 6/1993 | Purchio et al. | 435/69 |
| 5,238,950 | 8/1993 | Clader et al. | 514/360 |
| 5,242,397 | 9/1993 | Barath et al. | 604/96 |
| 5,268,358 | 12/1993 | Fretto | 514/12 |
| 5,280,016 | 1/1994 | Conrad et al. | 514/56 |
| 5,280,109 | 1/1994 | Miyazono et al. | 530/399 |
| 5,283,257 | 2/1994 | Gregory et al. | 514/458 |
| 5,284,763 | 2/1994 | Derynk et al. | 435/240 |
| 5,288,711 | 2/1994 | Mitchell et al. | 514/36 |
| 5,304,325 | 4/1994 | Kaufman et al. | 252/312 |
| 5,304,541 | 4/1994 | Purchio et al. | 514/12 |
| 5,308,622 | 5/1994 | Casscells et al. | 424/422 |
| 5,308,862 | 5/1994 | Ohlstein | 514/411 |
| 5,324,736 | 6/1994 | Magarian et al. | 514/317 |
| 5,326,757 | 7/1994 | Demopoulos | 514/167 |
| 5,356,713 | 10/1994 | Charmot et al. | 428/407 |
| 5,362,424 | 11/1994 | Lee et al. | 264/4.3 |
| 5,380,716 | 1/1995 | Conrad et al. | 514/56 |
| 5,385,935 | 1/1995 | Tamai et al. | 514/535 |
| 5,391,577 | 2/1995 | Cullinan et al. | 514/324 |
| 5,393,763 | 2/1995 | Black et al. | 514/333 |
| 5,453,436 | 9/1995 | Ohlstein | 514/411 |
| 5,468,746 | 11/1995 | Casagrande et al. | 514/235.5 |
| 5,472,985 | 12/1995 | Grainger et al. | 514/651 |
| 5,482,949 | 1/1996 | Black et al. | 514/324 |
| 5,491,173 | 2/1996 | Toivola et al. | 514/648 |

FOREIGN PATENT DOCUMENTS

| | | |
|---|---|---|
| 0260066 | 5/1990 | European Pat. Off. . |
| 2273873 | 6/1994 | United Kingdom . |
| 85/00107 | 1/1985 | WIPO . |
| WO91/15222 | 10/1991 | WIPO . |
| 91/15219 | 10/1991 | WIPO . |
| WO92/08480 | 5/1992 | WIPO . |
| WO92/18546 | 10/1992 | WIPO . |

OTHER PUBLICATIONS

Attwood et al., "A Light Scattering Study on Oil–In–Water Microemulsions", *International Journal of Pharmaceutics,* 52, 165–171 (1989).

Bagdade et al., "Effects of Tamoxifen Treatment on Plasma Lipids and Lipoprotein Lipid Composition", *J. Clinical Endocrinology and Metabolism,* 70, 1132–1135 (1990).

Barath et al., "Low Dose of Antitumor Agents Prevents Smooth Muscle Cell Proliferation After Endothelial Injury", *JACC,* 13, 252A, Abstract No. 252A (Feb. 1989).

Bertelli et al., "Adjuvant Tamoxifen in Primary Breast Cancer: Influence on Plasma Lipids and Antithrombin III Levels", *Breast Cancer Res. and Treatment,* 12, 307–310 (1988).

Bruengger et al., "Smooth Muscle Cell of the Canine Prostate in Spontaneous Benign Hyperplasia, Steroid Induced Hyperplasia and Estrogen or Tamoxifen Treated Dogs", *J. Urology,* 130, 1208–1210 (Dec. 1983).

(Abstract continued on next page.)

*Primary Examiner*—Raymond Henley, III
*Attorney, Agent, or Firm*—Schwegman, Lundberg, Woessner & Kluth, P.A.

[57] ABSTRACT

TGF-beta activators and TGF-beta production stimulators are employed to prevent or treat conditions characterized by inappropriate proliferation of smooth muscle cells, such as the prevention or reduction of restenosis following angioplasty or other vascular trauma. Such TGF-beta activators and production stimulators inhibit abnormal proliferation of smooth muscle cells. TGF-beta activators or production stimulators that are not characterized by an undesirable systemic toxicity profile at a prophylactic dose are also amenable to chronic use for prophylactic purposes with respect to disease states involving proliferation of vascular smooth muscle cells over time. Further provided is a method for upregulating cellular mRNA coding for TGF-beta.

18 Claims, 2 Drawing Sheets

OTHER PUBLICATIONS

Bruning et al., "Tamoxifen, Serum Lipoproteins and Cardiovascular Risk", *Br. J. Cancer*, 58, 497–499 (1988).

Butta et al., "Induction of Transforming Growth Factors $\beta_1$ in Human Breast Cancer in Vivo Following Tamoxifen Treatment ", *Cancer Res.*, 52, 4261–4264 (Aug. 1, 1992).

Craig et al., "Modern Pharmacology", *Little Brown and Company*, p. 399 (1982).

Dimond et al., "TGF–$\beta$ Shows Potential as Therapeutic Agent for Macular Holes", *Genetic Eng. News*, 7, 19 (Feb. 1, 1993).

Fanelli et al., "Restenosis Following Coronary Angioplasty", *Amer. Heart J.*, 119, 357–368 (Feb. 1990).

Farhat et al., "In Vitro Effect of Oestradiol on Thymidine Uptake in Pulmonary Vascular Smooth Muscle Cell: Role of the Endothelium", *Br. J. Pharamcol.*, 107, 679–683 (1992).

Fischer et al., "A Possible Mechanism in Arterial Wall for Mediation of Sex Difference in Atherosclerosis," *Experimental and Molecular Pathology*, 43, 288–296 (1985).

Forrester et al., "A Paradigm for Restenosis Based on Cell Biology: Clues for the Development of New Preventive Therapies", *JACC*, 17, 758–769 (Mar. 1, 1991).

Gasco et al., "In Vitro Permeation of Azelaic Acid From Viscoized Microemulsions", *Int'l J. of Pharmaceutics*, 69, pp. 193–196 (1991).

Grainger et al., "Hexamethylenebisacetamide Selectively Inhibits the Proliferation of Human and Rat Vascular Smooth–Muscle Cells", *Biochem J.*, 283, 403–408 (1992).

Grainger et al., "Tamoxifen Decreases the Rate of Proliferation of Rat Vascular Smooth Cells in Culture by Inducing the Production of Transforming Growth Factor b", *Biochem. J.*, 294, 109–112 (1993).

Grainger et al., "Proliferation of Human Smooth Muscle Cells Promoted by Lipoprotein (a)", *Science*, 260, 1655–1658 (1993).

Hanke et al., "Inhibition of Cellular Proliferation After Experimental Balloon Angioplasty by Low–Molecular––Weight Heparin", *Circulation*, 85, 1548–1556 (Apr. 1992).

Henriksson et al., "Hormonal Regulation of Serum Lp (a) Levels", *J. Clin. Invest.*, 89, 1166–1171 (Apr. 1992).

Hofmann et al., "Enhancement of the Antiproliferative Effect of cis Diamminedichloroplatinum(II) and Nitrogen Mustard by Inhibitors of Protein Kinase C", *Int. J. Cancer*, 42, 382–388 (1988).

Hwang et al., "Effects of Platelet–Contained Growth Factors (PDGF, EGF, IGF–1, and TGF–$\beta$) on DNA Synthesis in Porcine Aortic Smooth Muscle Cells in Culture", *Exp. Cell Res.*, 200, 358–360 (1992).

Jordan, "Long–Term Tamoxifen Therapy to Control or to Prevent Breast Cancer: Laboratory Concept to Clinical Trials", *Hormones Cell Biology and Cancer: Perspectives and Potentials;* Alan R. Liss, Inc.; pp. 105–123 (1988).

Kirschenlohr et al., "Adult human aortic smooth muscle cells in culture produce active TGF–$\beta$", *Am. J. Physiol.*, 261, C571–C576 (Aug. 1993).

Knabbe, C. et al., "Induction of Transforming Growth Factor $\beta$ by the Antiestrogens Droloxifene, Tamoxifen, and Toremifene in MCF–7 Cells", *Am. J. Clin. Oncol.*, 14, pp. S15–S20 (1991).

Koff et al., "Negative Regulation of G1 in Mammalian Cells: Inhibition of Cyclin E–Dependent Kinase by TGF–$\beta$", *Science*, 260, 536–538 (Apr. 23, 1993).

Lefer et al., "Mechanisms of the Cardioprotective Effect of Transforming Growth Factor $\beta_1$ Feline Myocardial Ischemia and Reperfusion", *PNAS* (USA), 90, 1018–1022 (Feb. 1993).

Lefer, "Role of Transforming Growth Factor $\beta$ is cardioprotection of the ischemic–reperfused myocardium", *Growth Factors and the Cardiovascular System*, P. Cummins, ed., Kluwer Acedemic Publishers, pp. 249–260 (1993).

Levy et al., "Drug Release From Submicronized O/W Emulsion: A New In Vitro Kinetic Evaluation Model", *International Journal of Pharmaceutics*, 66, 29–37 (1990).

Li et al., "Structure and Dynamics of Microemulsions Which Mimic the Lipid Phase of Low–Density Lipoproteins", *Biochimica et Biophysica Acta*, 1042, 42–50 (1990).

Liu et al, "Restenosis After Coronary Angioplasty–Potential Biologic Determinants and Role of Internal Hyperplasia", *Circulation*, 79, 1374–1387 (Jun. 1989).

Love et al., "Effects of Tamoxifen on Cardiovascular Risk Factors in Postmenopausal Women", *Annals of Internal Medicine*, 115, 860–864 (Dec. 1, 1991).

Love et al., "Effects of Tamoxifen Therapy on Lipid and Lipoprotein Levels in Postmenopausal Patients with Node–Negative Breast Cancer", *J. Natl. Cancer Inst.*, 82, 1327–1332 (Aug. 15, 1990).

McCaffrey et al., "Transforming Growth Factor–$\beta$ Activity is Potentiated by Heparin via Dissociation of the Transforming Growth Factor–$\beta/\alpha_2$–Macroglobulin Inactive Complex", *J. Cell Biol.*, 109, 441–448 (Jul. 1989).

McCague et al., "Synthesis of 4–Stannylated Tamoxifen Analogues; Useful Precursors to Radiolabelled Idoxifene and Aziridinyl 4–Iodotamoxifen", *J. Labelled Cmpds. Radiopharmaceuticals*, 34, 297–302 (1993).

McCaroll et al., "Preliminary Studies on the Regulation of Secretion of Latent Transforming Growth Factor–$\beta$ (TGF–$\beta$) by Endothelial Cells in Culture", *Clin. Chem.*, 36, p. 1152, Abstract No. 0934 (1990).

McDonald et al., "Fatal Myocardial Infarction in the Scottish Adjuvant Tamoxifen Trial", *B. Med. J.*, 303, 435–437 (Aug. 24, 1991).

Merrilees et al., "Synthesis of TGF–$\beta_1$ by Vascular Endothelial Cells is Correlated with Cell Spreading", *J. Vasc. Res.*, 29, 376–384 (1992).

Morisaki et al., "Effects of Transforming Growth Factor–$\beta_1$ on Growth of Aortic Smooth Muscle Cells: Influences of Interaction with Growth Factors, Cell State, Cell Phenotype, and Cell Cycle", *Atherosclerosis*, 88, 227–234 (1991).

Nikol et al., "Expression of Transforming Growth Factor–$\beta_1$ is Increased in Human Vascular Restenosis Lesions", *J. Clin. Invest.*, 1582–1592 (Oct. 1992).

Nolvadex Tamoxifene Citrate, ICI Pharma, 64033–02, Rev. L/07/92.

Pathak et al., "Enhanced Stability of Physostigmine Salicylate in Submicron O/W Emulsion", *International Journal of Pharmaceutics*, 65, 169–175 (1990).

Popma et al., "Factors Influencing Restenosis after Coronary Angioplasty", *Am. J. of Med.*, 88, 1–16N–1–24N (Jan. 1990).

Pouton, C. W., "Self–Emulsifying Drug Delivery Systems: Assessment of the Efficiency of Emulsification", *International Journal of Pharmaceutics*, 27, 335–348 (1985).

Rauterberg et al., "Collagens in Atherosclerotic Vessel Wall Lesions", *Current Topics in Pathology*, 87, 163–191 (1993).

Ross et al., "Chronic Inflammation, PDGF, TGFB, and Smooth Muscle Proliferation", *Molecular Mechanisms of Vascular Diseases*, p. 96 Abstract G 006. (1990).Ross, "The Pathogenesis of Atherosclerosis: A Perspective for the 1990s", *Nature*, 362, 801–809 (Apr. 29, 1993).

Schoenemanne et al., "The Differential Diagnosis of Spontaneous Pneumonthorax and Pulmonary Lymphangioleiomyomatosis Clinical Picture Diagnosis and Therapy", Chirug, 61, 301–303 (1990)—English Language Abstract Only. English abstract reported at 90, 432367 *Biosis* (1990).

Schwartz et al., "Restenosis After Balloon Angioplasty—A Practical Proliferative Model in Porcine Coronary Arteries", *Circulation*, 82, 2190–2200 (Dec. 1990).

Schwartz et al., "The Restenosis Paradigm Revisited: An Alternative Proposal for Cellular Mechanisms", *JACC*, 20, 1284–1293 (Nov. 1, 1992).

Shewmon et al., "Tamoxifen Lowers Lp(a) in Males with Heart Disease", *Supplement I Circulation*, 86, I–338, Abstract No. 1345, (Oct. 1992).

Snow et al., "Heparin modulates the composition of the extracellular matrix domain surrounding arterial smooth muscle cells", *Am. J. Path.*, 137, 313–330 (1990).

Steele et al., "Balloon Angioplasty–Natural History of the pathophysiological Response to Injury in a Pig Model", *Cir. Res.*, 57, 105–112 (Jul. 1985).

Streuli et al., "Extracellular Matrix Regulates Expression of the TGF-$\beta_1$ Gene", *J. of Cell Biol.*, 120, 253–260 (Jan. 1993).

T. R. Tice et al., "Biodegradable controlled–release parenteral systems", *Pharmaceutical Technology*, pp. 26–35, (Nov. 1984).

Vargas et al., "Oestradiol inhibits smooth muscle cell proliferation of Pig Coronary Artery", *Br. J. Pharmacol.* 109, 612–617 (1993).

Weissberg et al., "Approaches to the Development of Selective inhibitors of Vascular Smooth Muscle Cell Proliferation", *Cardiovascular Res.*, 27, 1191–1198 (1993).

Weissberg et al., "Effects of TGF-$\beta$ on Vascular Smooth Muscle Cell Growth", In: *Growth Factors and the Cardiovascular System*, P. Cummins, ed., Kluwer Academic Publishers, pp. 189–205 (1993).

Wolinsky et al., "Use of a Perforated Balloon Catheter to Deliver Concentrated Heparin Into the Wall of the Normal Canine Artery", *JACC*, 15, 475–481 (Feb. 1990).

Zuckerman et al., "Cytokine Regulation of Macrophage apo E Secretion: Opposing Effects of GM–CSF and TGF-$\beta$", *Atherosclerosis*, 96, 203–214 (1992).

R. K. Assoian, et al., "Type $\beta$ Transforming Growth Factor in Human Platelets: Release During Platelet Degranulation and Action of Vascular Smooth Muscle Cells", *J. Cell Biol*, 102, 1217–1223 (Apr., 1986).

S. K. Chander, et al., "Pyrrolidino–4–idotamoxifen and 4–idotamamoxifen New Analogues of the Antiestrogen Tamoxifen for the Treatment of Breast Cancer", *Cancer Res.*, 51, 5851–5858 (Nov., 1991).

D. J. Grainger, et al., "Effect of Tamoxifen in the Rat Carotid Injury Model In Vivo", Manuscript in Preparation, (1986).

P. C. Harpel, et al., "Plasmin Catalysis Binding of Lipoprotein (A) to Immobilized Fibrinogen and Fibrin.", *Proc. Natl. Acad. Sci. USA*, 86, 3847–3851 (1989).

N. Koyama, et al., "Regulation of Smooth Muscle Cells Migration by a New Autocrine Migration Factor and TGF-–beta", *Abstracts from the 64th Scientific Sessions*, II–459 (1989).

J. Massague, "The Transforming Growth Factor–B Family.", *Ann Rev. Cell Biol.*, 6, 597–641 (1990).

Z. Reiner, et al., "Antiestogen Tamoxifen Reduces Lipoprotein(a)". (1990).

S. Sedlacek, "Estrogenic Properties of Tamoxifen on Serum Lipids in Postmenopausal Women with Breast Cancer (BCA)", *Breast Cancer Research and Treatment*, 14, Abstract No. 82, p. 153 (1989).

L. M. Wakefield, et al., "Latent Transforming Growth Factor–$\beta$ from Human Platelets: A High Molecular Weight Complex Containing Precursor Sequences.", *J. Biol. Chem.*, 263, 7646–7654 (Jun., 1988).

R. L. Wilensky, et al., "Direct Intraarterial Wall Injection of Microparticles via a Catheter: A Potential Drug Delivery Strategy Following Angioplasty", *American Heart Journal*, 122, 1136–1140 (Oct., 1991).

Prevention of Coronary Heart Disease", *Avery's Drug Treatment—Principles and Practice of Clinical Pharmacology and Therapeutics*, Third Edition, Speight, T. M. (ed.), ADIS Press Limited, Auckland, New Zealand, pp. 594–595 (1987).

N. Koyama, et al., "Regulation of Smooth Muscle Cells Migration be a New Autocrine Migration Factor and TGF-$\beta$, *Circulation*, 84, II–459, Abstract 1829 (1991).

Z. Reiner, et al., "Antiestrogen Tamoxifen Reduces Lipoprotein (a)," Abstracts, The Second International Conference on Lipoprotein (a), New Orleans, LA, p. 124 (Nov. 12–14, 1992).

FIGURE 1

"A" connotes activation, and "I" connotes inhibition.

FIGURE 2

"A" connotes activation, and "I" connotes inhibition.

PREVENTION AND TREATMENT OF PATHOLOGIES ASSOCIATED WITH ABNORMALLY PROLIFERATIVE SMOOTH MUSCLE CELLS

This is a continuation of application Ser. No. 08/300,357, filed Sep. 2, 1994, now U.S. Pat. No. 5,472,985 which is a continuation of application Ser. No. 08/061,714, filed May 13, 1993, now abandoned.

FIELD OF THE INVENTION

This invention relates generally to the prevention and treatment of conditions characterized by abnormal smooth muscle cell proliferation. More specifically, mechanisms for in vivo vascular smooth muscle cell proliferation modulation and agents that impact those mechanisms are discussed.

BACKGROUND OF THE INVENTION

Many pathological conditions have been found to be associated with smooth muscle cell proliferation. Such conditions include restenosis, atherosclerosis, coronary heart disease, thrombosis, myocardial infarction, stroke, smooth muscle neoplasms such as leiomyoma and leiomyosarcoma of the bowel and uterus and uterine fibroid or fibroma. The mechanism of abnormal smooth muscle cell proliferation is not yet well understood.

For example, percutaneous transluminal coronary angioplasty (PTCA) is widely used as the primary treatment modality in many patients with coronary artery disease. PTCA can relieve-myocardial ischemia in patients with coronary artery disease by reducing lumen obstruction and improving coronary flow. The use of this surgical procedure has grown rapidly, with 39,000 procedures performed in 1983, nearly 150,000 in 1987, 200,000 in 1988, 250,000 in 1989, and over 500,000 PTCAs per year are estimated by 1994. Stenosis following PTCA remains a significant problem, with from 25% to 35% of the patients developing restenosis within 1 to 3 months. Restenosis results in significant morbidity and mortality and frequently necessitates further interventions such as repeat angioplasty or coronary bypass surgery. No surgical intervention or post-surgical treatment (to date) has proven effective in preventing restenosis.

The processes responsible for stenosis after PTCA are not completely understood but may result from a complex interplay among several different biologic agents and pathways. Viewed in histological sections, restenotic lesions may have an overgrowth of smooth muscle cells in the intimal layers of the vessel. Several possible mechanisms for smooth muscle cell proliferation after PTCA have been suggested.

Compounds that reportedly suppress smooth muscle proliferation in vitro may have undesirable pharmacological side effects when used in vivo. Heparin is an example of one such compound, which reportedly inhibits smooth muscle cell proliferation in vitro but when used in vivo has the potential adverse side effect of inhibiting coagulation. Heparin peptides, while having reduced anti-coagulant activity, have the undesirable pharmacological property of a short pharmacological half-life. Attempts have been made to solve such problems by using a double balloon catheter, i.e., for regional delivery of the therapeutic agent at the angioplasty site (e.g., U.S. Pat. No. 4,824,436), and by using biodegradable materials impregnated with a drug, i.e., to compensate for problems of short half-life (e.g., U.S. Pat. No. 4,929,602).

At least five considerations would, at first blush, appear to preclude use of inhibitory drugs to prevent stenosis resulting from overgrowth of smooth muscle cells. First, inhibitory agents may have systemic toxicity that could create an unacceptable level of risk for patients with cardiovascular disease. Second, inhibitory agents might interfere with vascular wound healing following surgery and that could either delay healing or weaken the structure or elasticity of the newly healed vessel wall. Third, inhibitory agents that kill smooth muscle cells could damage surrounding endothelium and/or other medial smooth muscle cells. Dead and dying cells also release mitogenic agents that might stimulate additional smooth muscle cell proliferation and exacerbate stenosis. Fourth, delivery of therapeutically effective levels of an inhibitory agent may be problematic from several standpoints, such as the following: a) delivery of a large number of molecules into the intercellular spaces between smooth muscle cells may be necessary to establish favorable conditions for allowing a therapeutically effective dose of molecules to cross the cell membrane; b) delivery of an inhibitory drug into the intracellular compartment where its action is exerted may be difficult to control; and c) optimizing the association of the inhibitory drug with its intracellular target (e.g., a ribosome) while minimizing intercellular redistribution of the drug (e.g,, to neighboring cells) may be difficult. Fifth, because smooth muscle cell proliferation takes place over several weeks it would appear a priori that the inhibitory drugs should also be administered over several weeks, perhaps continuously, to produce a beneficial effect.

As is apparent from the foregoing, many problems remain to be solved in the use of inhibitory drugs to effectively treat smooth muscle cell proliferation. It would be highly advantageous to develop new compositions or methods for inhibiting stenosis due to proliferation of vascular smooth muscle cells following, for example, traumatic injury to vessels rendered during vascular surgery.

SUMMARY OF THE INVENTION

TGF-beta activators and TGF-beta production stimulators may be employed in the practice of the present invention to prevent or treat conditions characterized by inappropriate proliferation of smooth muscle cells, such as the prevention or reduction of restenosis following angioplasty or other vascular trauma. Such TGF-beta activators and production stimulators inhibit abnormal proliferation of smooth muscle cells. A preferred TGF-beta activator/production stimulator is trans-2-[4-(1,2-diphenyl-1-butenyl)phenoxy]-N,N-dimethyl-ethylamine as well as functional equivalents, analogs or derivatives thereof.

The amount of TGF-beta activator or production stimulator administered is selected to treat vascular trauma of differing severity, with smaller doses being sufficient to treat lesser vascular trauma such as in the prevention of vascular rejection following graft or transplant. TGF-beta activators or production stimulators that are not characterized by an undesirable systemic toxicity profile at a prophylactic dose are also amenable to chronic use for prophylactic purposes with respect to disease states involving proliferation of vascular smooth muscle cells over time (e.g., atherosclerosis, coronary heart disease, thrombosis, myocardial infarction, stroke, smooth muscle neoplasms such as leiomyoma and leiomyosarcoma of the bowel and uterus, uterine fibroid or fibroma and the like). For prevention of restenosis, a large dose is preferably administered before or during the traumatic procedure (e.g., angioplasty). After the traumatic procedure is conducted, a series of smaller doses is administered over time to maintain an anti-proliferative effect for a time sufficient to substantially reduce the risk of or to prevent restenosis. A preferred therapeutic protocol duration for this purpose is from about 3 to about 26 weeks.

Further provided is a method for upregulating cellular mRNA coding for TGF-beta. Cells (e.g., smooth muscle cells) amenable to such metabolic manipulation are identified in the manner described herein and are exposed to an effective amount of a TGF-beta mRNA regulator (i.e., a subset of TGF-beta production stimulators). In this manner, TGF-beta production is stimulated, thereby inhibiting the abnormal proliferation of smooth muscle cells.

DETAILED DESCRIPTION OF THE INVENTION

As used herein the following terms have the meanings as set forth below:

"Proliferation," means an increase in cell number, i e., by mitosis of the cells.

"Abnormal or Pathological or Inappropriate Proliferation" means division, growth or migration of cells occurring more rapidly or to a significantly greater extent than typically occurs in a normally functioning cell of the same type.

"Expressed" means mRNA transcription and translation with resultant synthesis, glycosylation, and/or secretion of a polypeptide by a cell, e.g., CSPG synthesized by a vascular smooth muscle cell or pericyte.

"Tamoxifen" includes trans-2-[4-(1,2-diphenyl-1-butenyl)phenoxy]-N,N-dimethylethylamine which is capable of enhancing the production or activation of TGF-beta. The activated form of TGF-beta, in turn, inhibits vascular smooth muscle cell proliferation. Functional equivalents and derivatives of the aforementioned chemical compound are also included within the scope of the term "tamoxifen" for the purposes of this disclosure. Exemplary tamoxifen functional equivalents are plasmin, compounds capable of reducing the level or inactivating the lipoprotein Lp(a) or the glycoprotein apolipoprotein(a) and derivatives or analogs thereof. Tamoxifen is used herein as a prototypical TGF-beta activator/production stimulator.

"TGF-beta" includes transforming growth factor-beta as well as functional equivalents, derivatives and analogs thereof. TGF-beta is a polypeptide produced in a latent propeptide form having, at this time, no identified biological activity. To be rendered active and, therefore, capable of inhibiting vascular smooth muscle cell proliferation, the propeptide form of TGF-beta must be cleaved.

"TGF-beta activator" includes moieties capable of directly or indirectly activating the latent form of TGF-beta to the active form thereof. Plasmin, plasmin activators, tamoxifen as well as analogs, derivatives or functional equivalents thereof are exemplary TGF-beta activators useful in the practice of the present invention.

"TGF-beta production stimulator" includes moieties capable of directly or indirectly stimulating the production of TGF-beta (generally the latent form thereof). Such TGF-beta production stimulators may be TGF-beta mRNA regulators (i.e., moieties that increase the production of TGF-beta mRNA), enhancers of TGF-beta mRNA expression or the like.

"Direct" action implies that the TGF-beta activator acts on the latent form of TGF-beta. Such direct action of TGF-beta production stimulators indicates that cells upon which the production stimulate acts to increase TGF-beta mRNA production or expression of TGF-beta.

"Indirect" action implies that the TGF-beta activator acts on a moiety that itself or through one or more other moieties acts on latent TGF-beta. Such indirect action of TGF-beta production stimulators indicates that the stimulators act on a moiety that itself or through one or more other moieties acts on a population of cells to stimulate the production of TGF-beta mRNA or the expression of TGF-beta.

For the purposes of this description, the prototypical cells, upon which the effects of TGF-beta activators or production stimulators are felt, are smooth muscle cells and pericytes derived from the medial layers of vessels and adventitia vessels which proliferate in intimal hyperplastic vascular sites following injury, such as that caused during PTCA. TGF-beta activators and production stimulators are not restricted in use for therapy following angioplasty; rather, the usefulness thereof will be proscribed by their ability to inhibit abnormal cellular proliferation, for example, of smooth muscle cells and pericytes in the vascular wall. Thus, other aspects of the invention include TGF-beta activators or production stimulators used in early therapeutic intervention for reducing, delaying, or eliminating (and even reversing) atherosclerotic plaques and areas of vascular wall hypertrophy and/or hyperplasia. TGF-beta activators and production stimulators also find utility for early intervention in pre-atherosclerotic conditions, e.g., they are useful in patients at a high risk of developing atherosclerosis or with signs of hypertension resulting from atherosclerotic changes in vessels or vessel stenosis due to hypertrophy of the vessel wall.

TGF-beta activators or production stimulators of the invention are useful for inhibiting the pathological proliferation of vascular smooth muscle cells, e.g., for reducing, delaying, or eliminating stenosis following angioplasty. As used herein the term "reducing" means decreasing the intimal thickening that results from stimulation of smooth muscle cell proliferation following angioplasty, either in an animal model or in man. "Delaying" means delaying the time until onset of visible intimal hyperplasia (e.g., observed histologically or by angiographic examination) following angioplasty and may also be accompanied by "reduced" restenosis. "Eliminating" restenosis following angioplasty means completely "reducing" intimal thickening and/or completely "delaying" intimal hyperplasia in a patient to an extent which makes it no longer necessary to surgically intervene, i.e., to re-establish a suitable blood flow through the vessel by repeat angioplasty, atheroectomy, or coronary artery bypass surgery. The effects of reducing, delaying, or eliminating stenosis may be determined by methods routine to those skilled in the art including, but not limited to, angiography, ultrasonic evaluation, fluoroscopic imaging, fiber optic endoscopic examination or biopsy and histology.

High levels of lipoprotein Lp(a) are known to constitute a major risk factor for atherosclerosis, coronary heart disease and stroke. One symptom associated with such conditions and other problems, such as restenosis following balloon angioplasty and other pathogenic conditions is the proliferation or the migration of smooth muscle cells. No direct link between Lp(a) and proliferation of vascular smooth muscle cells had been established in the prior art.

Figure 1:
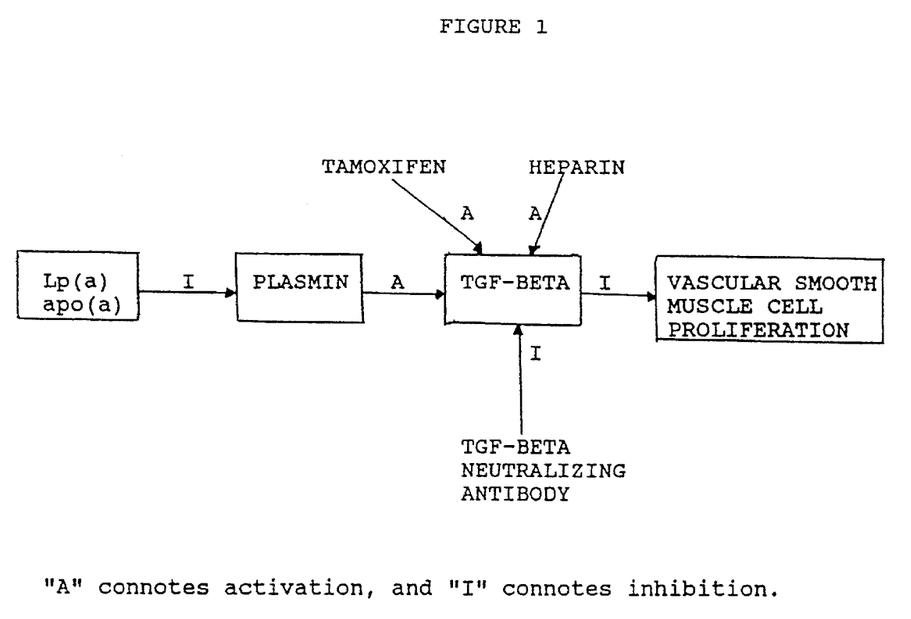
FIGS. 1 and 2 depict pathways for the modulation of vascular smooth muscle cell proliferation in vivo.

An in vivo pathway for the modulation of vascular smooth muscle cell proliferation is shown in FIG. 1. This mechanism is believed to constitute a portion of the mechanism that maintains vascular smooth muscle cells in a non-proliferative state in healthy vessels.

Vascular smooth muscle cell proliferation is inhibited by an active form of TGF-beta. Tamoxifen has been shown by the experimentation detailed in Example 1 hereof to stimulate both the production and the activation of TGF-beta. Heparin stimulates the activation of TGF-beta by affecting the release of the active form of TGF-beta from inactive complexes present in serum. TGF-beta neutralizing antibodies inhibit the activity of TGF-beta, thereby facilitating the proliferation of vascular smooth muscle cells. The apparent in vivo physiological regulator of the activation of TGF-beta is plasmin. Plasmin is derived from plasminogen through activation by, for example, tPA (tissue plasminogen activator). Plasminogen and, therefore, plasmin activity is inhibited by the lipoprotein Lp(a) or apolipoprotein(a) (apo(a)), thereby decreasing the activation of the latent form of TGF-beta and facilitating proliferation of vascular smooth muscle cells.

Figure 2:
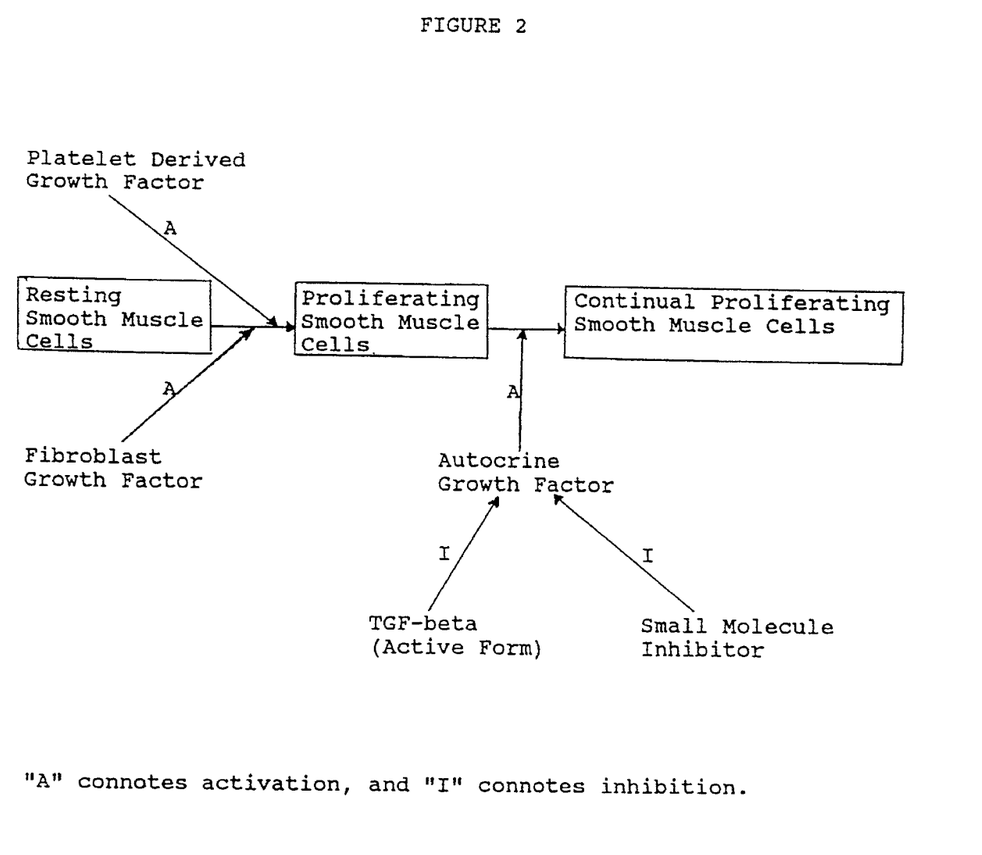

An additional pathway for the modulation of vascular smooth muscle cell proliferation is shown in FIG. 2. Resting smooth muscle cells constitute cells in their normal, quiescent non-proliferative state. Such resting smooth muscle cells may be converted to proliferating smooth muscle cells through activation by platelet derived growth factor (PDGF), fibroblast growth factor (FGF) or other stimulatory moieties. The proliferating smooth muscle cells may be converted to continual proliferating smooth muscle cells (i.e., smooth muscle cells capable of generating a pathological state resulting from over-proliferation thereof) by an autocrine growth factor. This growth factor is believed to be produced by proliferating smooth muscle cells. An increased level of autocrine growth factor, which can be inhibited by the active form of TGF-beta or an appropriately structured (i.e., designed) small molecule inhibitor, is believed to mediate the production of continual proliferating smooth muscle cells.

Lp(a) consists of low density lipoprotein (LDL) and apo(a). Apo(a) shares approximately 80% amino acid identity with plasminogen (see MacLean et al., *Nature*, 330: 132, 1987). Lp(a) has been found to inhibit cell-associated plasminogen activity (see, for example, Harpel et al., *Proc. Natl. Acad. Sci, USA*, 86: 3847, 1989). Experiments conducted on human aortic vascular smooth muscle cells derived from healthy transplant donor tissue, cultured in Dulbecco's modified Eagles medium (DMEM)+10% fetal calf serum (FCS) as described in Grainger et al., *Biochem. J.*, 283: 403, 1992, indicated the following:

1) Addition of Lp(a) to sub-confluent human vascular smooth muscle cells stimulated their proliferation in a dose dependent manner (addition of 500 nM Lp(a) to human vascular smooth muscle cells caused a reduction in doubling time from 82±4 hours to 47±4 hours);
2) Addition of apo(a) had a similar effect, although a higher concentration of apo(a) appeared to be required therefor;
3) Addition of LDL at varying concentrations up to 1 micromolar had no effect on proliferation.

One possible mode of action for Lp(a) and apo(a) is competitive inhibition of surface-associated plasminogen activation and the subsequent activation of TGF-beta by plasmin. TGF-beta is a potent growth inhibitor of a number of anchorage-dependent cells, including smooth muscle cells. TGF-beta is produced as a latent propeptide having a covalently linked homodimer structure in which the active moiety is non-covalently linked to the amino-terminal portion of the propeptide. Latent TGF-beta must be cleaved (e.g., in vitro by acid treatment or in vivo by the serine protease plasmin) in order to become capable of inhibiting the proliferation of vascular smooth muscle cells. Plasmin is therefore a leading candidate to be a physiological regulator of TGF-beta.

The hypothesis that Lp(a) and apo(a) were acting on cultured human vascular smooth muscle cells by interfering with activation of latent TGF-beta was tested. In support of this hypothesis, an observation was made that plasmin activity associated with vascular smooth muscle cells was reduced 7-fold by Lp(a) and 5-fold by apo(a). The plasmin activity in the conditioned medium was also reduced by Lp(a) and apo(a) by about 2-fold, but was much lower than cell-associated plasmin activity in vascular smooth muscle cell cultures. These observations are consistent with previous findings that Lp(a) is a more potent inhibitor of surface-associated, rather than fluid phase, plasminogen activation.

To exclude the possibility that Lp(a) was affecting the synthesis of plasminogen activators rather than plasminogen activation, plasminogen activator levels in human vascular smooth muscle cell cultures were measured in the presence and absence of the lipoproteins and in the presence of a large excess of plasminogen, so that the lipoproteins present would not significantly act as competitive inhibitors. Total plasminogen activator activity was not affected by the presence of any of the lipoproteins in the vascular smooth muscle cell cultures. For example, plasminogen activator activity in the conditioned medium remained at 0.7±0.6 mU/ml with Lp(a) additions up to 500 nM.

Lp(a) and apo(a) both reduced the level of active TGF-beta by more than 100-fold compared to control or LDL-treated cultures. The level of total latent plus active TGF-beta measured by ELISA as described in Example 1 was unaffected by the presence of Lp(a) or apo(a), however. These facts lead to the conclusion that Lp(a) stimulates proliferation of human vascular smooth muscle cells by inhibiting plasmin activation of latent TGF-beta to active TGF-beta.

To further test this conclusion and exclude the possibility that Lp(a) was acting by binding active TGF-beta as well as reducing plasmin activity, human vascular smooth muscle cells were cultured in the presence of Lp(a). These cells had a population doubling time of 47±3 hours. Addition of plasmin was able to overcome the population doubling time reducing effect of Lp(a) and reduce the cell number to control levels, with the population doubling time increased to 97±4 hours.

The role of plasmin in the pathway was confirmed by studies in which inhibitors of plasmin activity were added to human vascular smooth muscle cells. Like Lp(a), these protease inhibitors increased cell number. Aprotinin, for example, decreased the population doubling time from 82±4 hours in control cultures to 48±5 hours, and alpha2-antiplasmin decreased the population doubling time to 45±2 hours. 500 nM Lp(a) and aprotinin addition resulted in only a slight additional stimulation of proliferation, with the population doubling time for cultures of this experiment being 45±6 hours. Neutralizing antibodies to TGF-beta similarly decreased population doubling time in vascular smooth muscle cells (see, for example, Example 1). In summary, Lp(a), plasmin inhibitors and neutralizing antibody to TGF-beta stimulate proliferation of vascular smooth muscle cells, while plasmin nullifies the growth stimulation of Lp(a). These results support the theory that the mode of action of Lp(a) and apo(a) is the competitive inhibition of plasminogen activation.

Experimentation conducted to ascertain the impact of tamoxifen on TGF-beta and vascular smooth muscle cell proliferation is set forth in detail in Example 1. The results of those experiments are summarized below.

1) Addition of tamoxifen decreased the rate of proliferation, with maximal inhibition observed at concentrations above 33 micromolar. 50 micromolar tamoxifen concentrations produced an increase in cell number (96 hours following the addition of serum) that was reduced by 66%±5.2% (n=3).

2) Tamoxifen did not significantly reduce the proportion of cells completing the cell cycle and dividing. Inhibition of vascular smooth muscle cells caused by tamoxifen therefore appears to be the result of an increase in the cell cycle time of nearly all (>90%) of the proliferating cells.

3) Tamoxifen decreases the rate of proliferation of serum-stimulated vascular smooth muscle cells by increasing the time taken to traverse the $G_2$ to M phase of the cell cycle.

4) Tamoxifen decreased the rate of proliferation of vascular smooth muscle cells by inducing TGF-beta activity.

5) Vascular smooth muscle cells produced TGF-beta in response to tamoxifen. Tamoxifen appears to increase TGF-beta activity in cultures of rat vascular smooth muscle cells by stimulating the production of latent TGF-beta and increasing the proportion of the total TGF-beta which has been activated.

6) Tamoxifen, unlike heparin, does not act by releasing TGF-beta from inactive complexes present in serum.

7) TGF-beta1EA was increased by approximately 10-fold by 24 hours after addition of tamoxifen (10 micromolar). This result suggests that the expression of TGF-beta mRNA by the smooth muscle cells will be increased, thereby facilitating decreased proliferation thereof by activated TGF-beta. This mechanism can be exploited using cells incorporating nucleic acids encoding TGF-beta mRNA, which cells are identifiable by persons skilled in the art employing known techniques.

8) Tamoxifen is a selective inhibitor of vascular smooth muscle proliferation with an $ED_{50}$ at least 10-fold lower for vascular smooth muscle cells than for adventitial fibroblasts.

Additional experimentation has shown that the addition of Lp(a) or apo(a) substantially reduced the vascular smooth muscle cell proliferation inhibitory activity of tamoxifen, with the population doubling time in the presence of tamoxifen and Lp(a) being 42±2 hours. Also, the presence of Lp(a) reduced the levels of active TGF-beta produced in response to the addition of tamoxifen by about 50-fold. Addition of plasmin to rat vascular smooth muscle cells treated with tamoxifen and Lp(a) resulted in most of the TGF-beta being activated, and proliferation was again slowed (with the population doubling time being 57±3 hours). These observations are consistent with the theory that Lp(a) acts by inhibiting TGF-beta activation.

Identification of therapeutic agents (direct or indirect TGF-beta activators or production stimulators) that act to inhibit vascular smooth muscle cell proliferation by the pathway shown in FIG. 1 can be identified by a practitioner in the art by conducting experiments of the type described above and in Example 1. Such experimental protocols facilitate the identification of therapeutic agents useful in the practice of the present invention and capable of one of the following activities:

1) production or activation of TGF-beta;
2) having TGF-beta activity;
3) activation of plasmin;
4) activation of plasminogen; and
5) reduction of Lp(a) or apo(a) level.

Identification of therapeutic agents (direct or indirect TGF-beta activators or production stimulators) that act to inhibit vascular smooth muscle cell proliferation by the pathway shown in FIG. 2 can be identified by a practitioner in the art by conducting experimentation using known techniques that is designed to identify growth factors made by proliferating smooth muscle cells, which growth factors also act on those cells (i.e., autocrine growth factors). Known techniques for rational drug design are then used to screen small molecules for the ability to inhibit the production or activity of such autocrine growth factors. Such experimental protocols facilitate the identification of therapeutic agents useful in the practice of the present invention and capable of one of the following activities:

1) production or activation of TGF-beta;
2) having TGF-beta activity; and
3) inhibit the activity or production of an autocrine growth factor produced by proliferating smooth muscle cells.

Smooth muscle cell proliferation is a pathological factor in myocardial infarctions, atherosclerosis, thrombosis, restenosis and the like. Therapeutic/prophylactic agents of the present invention, including tamoxifen and the like, having at least one of the activities recited above and therefore being capable of inhibiting proliferation of vascular smooth muscle cells, are useful in the prevention or treatment of these conditions. Manipulation of the proliferation modulation pathway for vascular smooth muscle cells to prevent or reduce such proliferation removes or reduces a major component of the arterial lesions of atherosclerosis and the restenosed arteries following angioplasty, for example.

More specifically, chronically maintaining an elevated level of activated TGF-beta reduces the probability of atherosclerotic lesions forming as a result of vascular smooth muscle cell proliferation. Consequently, administration of TGF-beta activators or TGF-beta production stimulators protects against atherosclerosis and subsequent myocardial infarctions that are consequent to coronary artery blockage. Also, substantially increasing the activated TGF-beta level for a short time period allows a recipient to at least partially offset the strong stimulus for vascular smooth muscle cell proliferation caused by highly traumatic injuries or procedures such as angioplasty. Continued lower dose delivery to the traumatized site further protects against restenosis resulting from vascular smooth muscle cell proliferation in the traumatized area.

Tamoxifen, for example, is commercially available from ICI Pharmaceuticals (Macclesfield, England). The prevalent commercially available form is a 10 mg tablet. Such tablets or portions thereof can be employed in the prophylactic and treatment protocols described herein.

Prevention or treatment relating to a traumatized or diseased vascular site, for example, the TGF-beta activators or production stimulators may also be administered in accordance with the present invention using an infusion catheter, such as produced by C. R. Bard Inc., Billerica, Mass., or that disclosed by Wolinsky (7; U.S. Pat. No. 4,824,436) or Spears (U.S. Pat. No. 4,512,762). In this case, a therapeutically/prophylactically effective dosage of the TGF-beta activator or production stimulator will be typically reached when the concentration thereof in the fluid space between the balloons of the catheter is in the range of about $10^{-3}$ to $10^{-12}$M. It is recognized by the present inventors that TGF-beta activators or stimulators may only need to be delivered in an anti-proliferative therapeutic/prophylactic dosage sufficient to expose the proximal (6 to 9) cell layers of the intimal or tunica media cells lining the lumen thereto. Also, such a dosage can be determined empirically, e.g., by a) infusing vessels from suitable animal model systems and using immunohistochemical methods to detect the TGF-beta activator or production stimulator and its effects; and b) conducting suitable in vitro studies.

It will be recognized by those skilled in the art that desired therapeutically/prophylactically effective dosages of a TGF-beta activator or production stimulator administered by a catheter in accordance with the invention will be dependent on several factors, including, e.g.: a) the atmospheric pressure applied during infusion; b) the time over which the TGF-beta activator or production stimulator administered resides at the vascular site; c) the nature of the therapeutic or prophylactic agent employed; and/or d) the nature of the vascular trauma and therapy desired. Those skilled practitioners trained to deliver drugs at therapeutically or prophylactically effective dosages (e.g., by monitoring drug levels and observing clinical effects in patients) will determine the optimal dosage for an individual patient based on experience and professional judgment. In a preferred embodiment, about 0.3 atm (i.e., 300 mm of Hg) to about 5 atm of pressure applied for 15 seconds to 3 minutes directly to the vascular wall is adequate to achieve infiltration of a TGF-beta activator or production stimulator into the smooth muscle layers of a mammalian artery wall. Those skilled in the art will recognize that infiltration of the TGF-beta activator or production stimulator into intimal layers of a diseased human vessel wall will probably be variable and will need to be determined on an individual basis.

While two representative embodiments of the invention relate to prophylactic or therapeutic methods employing an oral dosage for or infusion catheter administration, it will be recognized that other methods for drug delivery or routes of administration may also be useful, e.g., injection by the intravenous, intralymphatic, intrathecal, intraarterial, local delivery by implanted osmotic pumps or other intracavity routes. Administration of TGF-beta activators or production stimulators in accordance with the present invention may be continuous or intermittent, depending, for example, upon the recipient's physiological condition, whether the purpose of the administration is therapeutic or prophylactic and other factors known to skilled practitioners.

In the practice of certain embodiments of the present invention, catheter and other administration routes are preferably conducted using a TGF-beta activator or production stimulator dispersed in a pharmaceutically acceptable carrier that is in liquid phase. Useful pharmaceutically acceptable carriers include generally employed carriers, such as phosphate buffered saline solution, water, emulsions (e.g., oil/water and water/oil emulsions) and wetting agents of various types.

For TGF-beta activators or production stimulators, such as tamoxifen, several exemplary dosing regimens are contemplated, depending upon the condition being treated and the stage to which the condition has progressed. For prophylactic purposes with respect to atherosclerosis, for example, a low chronic dose sufficient to elevate in vivo TGF-beta production is contemplated. An exemplary dose of this type is about 0.1 mg/kg/day (ranging between about 0.1 and about 10 mg/kg/day). Another exemplary dose range is from about 0.01 to about 1000 micrograms/ml. Such low doses are also contemplated for use with respect to ameliorating stenosis following relatively low trauma injury or intervention, such as vein grafts or transplants or organ allografts, for example. No adverse side effects (e.g., nausea as experienced by recipients of higher dose administrations when tamoxifen has been employed in the treatment of breast cancer) are anticipated with respect to these chronic or low dosing regimens.

For prevention of restenosis following angioplasty, an example of a higher trauma injury or intervention resulting in a stronger acute proliferative stimulus to smooth muscle cells, a higher dose would be required. For example, a dosing regimen is contemplated which involves a single "pre-loading" dose (or multiple, smaller pre-loading doses) given before or at the time of the intervention, with a chronic smaller (follow up) dose delivered daily for two to three weeks or longer following intervention. For example, a single pre-loading dose may be administered about 24 hours prior to intervention, while multiple preloading doses may be administered daily for several days prior to intervention. An exemplary single pre-loading dose is about 50 mg/kg (ranging between about 10 and about 1000 mg/kg), while an exemplary multiple pre-loading individual dose is about 10 mg/kg/day (ranging between about 0.01 and 10 mg/kg/day).

It will be recognized that where the TGF-beta activator or production stimulator is to be delivered with an infusion catheter, the therapeutic dosage required to achieve the desired inhibitory activity can be anticipated through the use of in vitro studies. In a preferred aspect, the infusion catheter may be conveniently a double balloon or quadruple balloon catheter with a permeable membrane. In one representative embodiment, a therapeutically effective dosage of a TGF-beta activator or production stimulator is useful in treating vascular trauma resulting from disease (e.g., atherosclerosis, aneurysm, or the like) or vascular surgical procedures such as angioplasty, atheroectomy, placement of a stent (e.g., in a vessel), thrombectomy, and grafting. Atheroectomy may be performed, for example, by surgical excision, ultrasound or laser treatment, or by high pressure fluid flow. Grafting may be, for example, vascular grafting using natural or synthetic materials or surgical anastomosis of vessels such as, e.g., during organ grafting. Those skilled in the art will recognize that the appropriate therapeutic dosage for a given vascular surgical procedure (above) is determined in in vitro and in vivo animal model studies, and in human preclinical trials.

While two representative embodiments of the invention relate to therapeutic methods employing an oral dosage for or infusion catheter administration, it will be recognized that other methods for drug delivery or routes of administration may also be useful, e.g., injection by the intravenous, intralymphatic, intrathecal, intraarterial, local delivery by implanted osmotic pumps or other intracavity routes. Administration of TGF-beta activators or production stimulators in accordance with the present invention may be continuous or intermittent, depending, for example, upon the recipient's physiological condition, whether the purpose of the administration is therapeutic or prophylactic and other factors known to skilled practitioners.

In the practice of certain embodiments of the present invention, catheter and other administration routes are preferably conducted using a TGF-beta activator or production stimulator dispersed in a pharmaceutically acceptable carrier that is in liquid phase. Useful pharmaceutically acceptable carriers include the generally employed carriers, such as phosphate buffered saline solution, water, emulsions (e.g., oil/water and water/oil emulsions) and wetting agents of various types.

The invention will be better understood by making reference to the following specific example.

EXAMPLE 1

Impact of Tamoxifen on Vascular Smooth Muscle Cells and the Relationship thereof to TGF-Beta Production and Activation Cell culture, DNA synthesis assay and cell counting. Rat vascular smooth muscle cells were cultured after enzymatic dispersion of the aortic media from 12–17 week old Wistar rats as described in Grainger et al., *Biochem. J.*, 277: 145–151, 1991. When the cells reached confluence (after about 6 days) the cells were released with trypsin/EDTA (available from Gibco) and diluted 1:2 in Dulbecco's modification of Eagle's medium (DMEM; available from ICN/Flow) supplemented with 100 U/ml penicillin and 10% fetal calf serum (FCS). The cells were then replated on tissue culture plastic (available from ICN/Flow) at approximately $1 \times 10^4$ cells/cm$^2$. The cells were subcultured repeatedly in this way when confluence was attained (about every 4 days), and the cells were used between passages 6 and 12.

Rat adventitial fibroblasts were cultured as described in Grainger et al., *Biochem. J.*, 283: 403–408, 1992. Briefly, the aortae were treated with collagenase (3 mg/ml) for 30 minutes at 37° C. The tunica adventitia was stripped away from the media. The adventitia was dispersed for 2 hours in elastase (1 mg/ml) and collagenase (3 mg/ml) dissolved in medium M199 (available from ICN/Flow). The cells were then spun out (900×g, 3 minutes), resuspended in DMEM+ 10% FCS and plated out at $8 \times 10^4$ cells/cm$^2$ on tissue culture plastic. When the cells reached confluence (after about 10 days), they were subcultured as described for vascular smooth muscle cells. Adventitial fibroblasts were subcultured every 3 days at 1:3 dilution and used between passages 3 and 9.

DNA synthesis was assayed by [$^3$H]-thymidine incorporation as described in Grainger et al., *Biochem, J.*, 277:145–151, 1991. Vascular smooth muscle cells were subcultured, grown in DMEM+10% FCS for 24 hours, made quiescent in serum-free DMEM for 48 hours and restimulated with 10% FCS at "0" hours. [$^3$H]-thymidine (5 microcuries/ml; available from Amersham International) was added 12 hours after restimulation and the cells were harvested after 24 hours. DNA synthesis by adventitial fibroblasts was determined similarly, except that the cells were made quiescent in serum-free DMEM for 24 hours.

Cells were prepared for counting by hemocytometer from triplicate culture dishes as described in Grainger et al., *Biochem. J.*, 277:145–151, 1991. Cells were also counted by direct microscopic observation of gridded culture dishes. The grids were scored into the plastic on the inner surface, so that the cells could not migrate into or out of the area being counted during the experiment. Cells in each of four squares in two separate wells were counted at each time point. All cell counting experiments were repeated on at least three separate cultures.

A stock solution of tamoxifen (5 mM; available from ICI Pharmaceuticals) was made up in 10% ethanol (EtOH) and diluted in DMEM and 10% FCS to give the final concentration. The effects of each tamoxifen concentration were compared with the effects observed in control wells containing the same final concentration of the ethanol vehicle.

Recombinant TGF-beta (available from Amersham International) was dissolved in 25 mM Tris/Cl to give a 5 microgram/ml stock solution and sterile filtered through a Spinnex Tube (such as a Centrex Disposable Microfilter Unit available from Rainin Instrument Company, Inc., Woburn, Mass.). Neutralizing antiserum to TGF-beta (BDA19; available from R & D Systems) was reconstituted in sterile MilliQ water (available from Millipore Corporation, Bedford, Mass.). At 10 micrograms/ml, this antibody completely abolished the activity of 10 ng/ml recombinant TGF-beta on subcultured (8th passage) vascular smooth muscle cells.

Assays for TGF-Beta. The TGF-beta activity present in medium conditioned on various cells was determined by DNA synthesis assay on mink lung endothelial (MvLu) cells; a modification of the assay described in Danielpour et al., *J. Cell. Physiol.*, 138: 79–83, 1989. MvLu cells were subcultured at 1:5 dilution in DMEM+10% FCS. After 24 hours, the medium was replaced with the conditioned medium to be tested in the absence or presence of the neutralizing antiserum to TGF-beta at 10 micrograms/ml. DNA synthesis during a 1 hour pulse of [$^3$H]-thymidine (5 microcuries/ml) was determined 23 hours after addition of the test medium. TGF-beta activity was calculated as the proportion of the inhibition of DNA synthesis which was reversed in the presence of neutralizing antibody, using a standard curve to convert the inhibition values into quantities of TGF-beta. The TGF-beta1 standards and conditioned media both contained 10% FCS in DMEM.

The total latent and active TGF-beta present was determined by a sandwich ELISA. Maxisorb 96-well ELISA plates (available from Gibco) were coated with neutralizing antiserum against TGF-beta (BDA19; available from R & D Systems) at 2 micrograms/cm$^2$ in phosphate buffered saline (PBS) overnight at room temperature. The plates were washed between each step with tris-buffered saline containing 0.1% Triton X-100 (available from Sigma Chemical Company). The plates were incubated with samples for 2 hours, with a second antibody to TGF-beta (BDA5; available from R & D Systems) at 0.1 micrograms/ml for 2 hours, anti-rabbit IgG peroxidase conjugated to antibody (available from Sigma Chemical Co.), made up according to manufacturer's instructions, for 15 minutes. Absorbances at 492 nm were converted into quantities of TGF-beta protein using a standard curve. Both conditioned media and standards were assayed in the presence of 10% FCS in DMEM. This assay was linear for TGF-beta concentrations in the range from 0.1 ng/ml to 20 ng/ml in the presence of 10% FCS in DMEM.

RNA Preparation and Northern Analysis. Total cytoplasmic RNA was isolated from cultured vascular smooth muscle cells as described in Kemp et al., *Biochem. J.*, 277: 285–288, 1991. Northern analysis was performed by electrophoresis of total cytoplasmic RNA in 1.5% agarose gels in a buffer containing 2.2M formaldehyde, 20 mM 3-(N-morpholino)propanesulfonic acid, 1 mM EDTA, 5 mM sodium acetate and 0.5 micrograms/ml ethidium bromide. The integrity of the RNA was checked by visualizing the gel under UV illumination prior to transfer onto Hybond N (available from Pharmacia LKB) as specified by the manufacturer. Filters were hybridized as described in Kemp et al., *Biochem, J.*, 277: 285–288, 1991, using a [$^{32}$P]-oligolabeled mouse TGF-beta1 probe corresponding to amino acids 68–228 in the precursor region of the TGF-beta1 polypeptide as set forth in Millan et al., *Development*, 111: 131–144.

Results. Vascular smooth muscle cells from the aorta of adult rats proliferate with a cell cycle time of approximately 35 hours in DMEM+10% FCS (see, for example, Grainger et al., *Biochem. J.*, 277: 145–151, 1991). Addition of tamoxifen decreased the rate of proliferation with maximal inhibition at concentrations above 33 micromolar. 50 micromolar tamoxifen concentrations produced an increase in cell number (96 hours following the addition of serum) that was reduced by 66%±5.2% (n=3). The slower rate of proliferation was hypothesized to stem from a complete blockage of proliferation for a proportion of the vascular smooth muscle cells or from an increase in the cell cycle time of all of the cells. To distinguish between these possibilities, the proportion of the cells passing through M phase and the time course of entry into cell division were determined.

Quiescent vascular smooth muscle cells were stimulated with DMEM+10% FCS in the absence or presence of 33 micromolar tamoxifen, with the cell number being determined at 8 hour intervals by time lapse photomicroscopy. In the presence of ethanol vehicle alone, more than 95% of the vascular smooth muscle cells had divided by 40 hours, whereas there was no significant increase in cell number in the presence of tamoxifen until after 48 hours. By 64 hours, however, more than 90% of the cells had divided in the presence of tamoxifen. The time taken for 50% of the cells to divide after stimulation by serum was increased from 35±3 hours (n=7) to 54±2 hours (n=3) by 33 micromolar tamoxifen. Since tamoxifen did not significantly reduce the proportion of cells completing the cell cycle and dividing, inhibition of vascular smooth muscle cells caused by tamoxifen appears to be the result of an increase in the cell cycle time of nearly all (>90%) of the proliferating cells.

To determine whether tamoxifen increased the duration of the cell cycle of vascular smooth muscle cells by increasing the duration of the $G_0$ to S phase, the effect of tamoxifen on entry into DNA synthesis was analyzed. Tamoxifen at concentrations up to 50 micromolar did not significantly affect the time course or the proportion of cells entering DNA synthesis following serum stimulation of quiescent vascular smooth muscle cells (DNA synthesis between 12 hours and 24 hours after stimulation was measured by [$^3$H]-thymidine incorporation: control at 17614±1714 cpm; 10 micromolar tamoxifen at 16898±3417 cpm; and 50 micromolar tamoxifen at 18002±4167 cpm). Since the duration of S phase is approximately 12 hours (unpublished data), tamoxifen does not appear to have significantly impacted the time course of entry into DNA synthesis. These results therefore imply that tamoxifen decreases the rate of proliferation of serumstimulated vascular smooth muscle cells by increasing the time taken to traverse the $G_2$ to M phase of the cell cycle.

Based upon these results, it appeared that tamoxifen exhibited effects similar to those previously described for TGF-beta (see, for example, Assoian et al., *J. Cell. Biol.*, 109: 441–448, 1986) with respect to proliferation of subcultured vascular smooth muscle cells in the presence of serum. Tamoxifen is known to induce TGF-beta activity in cultures of breast carcinoma cell lines as described, for example, in Knabbe, et al., *Cell*, 48: 417–425, 1987. consequently, experimentation was conducted to determine whether tamoxifen decreased the rate of proliferation of vascular smooth muscle cells by inducing TGF-beta activity. When quiescent vascular smooth muscle cells were stimulated with 10% FCS in the presence of 50 micromolar tamoxifen and 10 micrograms/ml neutralizing antiserum against TGF-beta, the cells proliferated at the same rate as control cells in the presence of ethanol vehicle alone.

To confirm that the vascular smooth muscle cells produced TGF-beta in response to tamoxifen, such cells were treated with tamoxifen for 96 hours in the presence of 10% FCS. The conditioned medium was then collected and TGF-beta activity was determined by the modified mink lung epithelial (MvLu) cell assay described above. Tamoxifen increased the TGF-beta activity in the medium by >50-fold. Addition of tamoxifen (50 micromolar) in fresh DMEM+10% FCS to the MvLu cells had no effect on DNA synthesis, demonstrating that tamoxifen did not induce production of active TGF-beta by the MvLu cells.

TGF-beta is produced as a latent propeptide which can be activated outside the cell by proteases such as plasmin. To determine whether tamoxifen increased TGF-beta activity by promoting the activation of latent TGF-beta or by stimulating the production of the latent propeptide which was subsequently activated, the total latent plus active TGF-beta present in the conditioned medium was determined by sandwich ELISA as described above. After 96 hours in the presence of tamoxifen (50 micromolar), the total TGF-beta protein present was increased by approximately 4-fold. Furthermore, the proportion of the TGF-beta present in active form was increased from <5% in the medium conditioned on vascular smooth muscle cells in the presence of ethanol vehicle alone to approximately 35% in the medium conditioned on cells treated with tamoxifen. Thus, tamoxifen appears to increase TGF-beta activity in cultures of rat vascular smooth muscle cells by stimulating the production of latent TGF-beta and increasing the proportion of the total TGF-beta which has been activated.

Heparin increases TGF-beta activity in medium conditioned on vascular smooth muscle cells (unpublished data). The mechanism of action of heparin in this regard appears to involve the release of TGF-beta from inactive complexes present in serum, because pretreatment of serum with heparin immobilized on agarose beads is as effective as direct addition of free heparin to the cells. To determine whether tamoxifen acts to release TGF-beta from sequestered complexes in serum which are not immunoreactive in the ELISA assay, 10% FCS+ DMEM was treated with 50 micromolar tamoxifen for 96 hours at 37° C. in the absence of cells. Medium treated in this way contained similar levels of TGF-beta protein and activity to untreated medium. It appears, therefore, that tamoxifen, unlike heparin, does not act by releasing TGF-beta from inactive complexes present in serum.

The content of TGF-beta1 mRNA was also analyzed by Northern analysis at various time points after addition of tamoxifen. Subcultured rat vascular smooth muscle cells (6th passage in exponential growth) in the absence or presence of ethanol vehicle alone contain very little mRNA for TGF-beta1. By 24 hours after addition of tamoxifen (10 micromolar), TGF-beta1 mRNA was increased approximately 10-fold.

Although TGF-beta decreases the rate of proliferation of vascular smooth muscle cells, it does not affect the rate of proliferation of fibroblasts. Tamoxifen at concentrations of up to 50 micromolar did not reduce the rate of proliferation of subcultured adventitial fibroblasts. Tamoxifen is therefore a selective inhibitor of vascular smooth muscle proliferation with an $ED_{50}$ at least 10-fold lower for vascular smooth muscle cells than for adventitial fibroblasts.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A therapeutic method to treat procedural vascular trauma, comprising orally administering to a mammal subjected to the vascular trauma an amount of an agent effective upon oral administration to elevate the level of TGF-beta so as to inhibit the pathological proliferation of vascular smooth muscle cells.

2. The therapeutic method of claim 1 wherein stenosis or restenosis of a mammalian blood vessel is reduced or inhibited.

3. The therapeutic method of claim 1 wherein the procedural vascular trauma is due to a graft or transplant procedure.

4. The therapeutic method of claim 1 wherein the procedural vascular trauma is angioplasty.

5. The therapeutic method of claim 1 wherein the agent increases the cell cycle time of the smooth muscle cells.

6. The therapeutic method of claim 1 wherein the agent elevates the level of TGF-beta by increasing production of TGF-beta mRNA.

7. The therapeutic method of claim 1 comprising administering a series of doses of the agent effective to maintain an elevated level of TGF-beta.

8. The method of claim 7 wherein the TGF-beta which is elevated is active TGF-beta.

9. The therapeutic method of claim 1 wherein the agent comprises trans-2-[4-1,2-diphenyl-1-butenyl)phenoxy]-N,N-dimethyl-ethylamine or an analog thereof.

10. The therapeutic method of claim 1 wherein the agent does not include heparin or a heparin peptide.

11. A method for reducing or inhibiting restenosis associated with an angioplasty procedure, which method comprises orally administering to a mammal an amount of an agent effective upon oral administration to elevate levels of TGF-beta.

12. The method of claim 11 wherein the agent is effective to elevate the level of active TGF-beta.

13. The method of claim 11 wherein the agent comprises trans-2-[4-(1,2-diphenyl-1-butenyl)phenoxy]-N,N-dimethyl-ethylamine or an analog thereof.

14. The method of claim 11 wherein the agent does not include heparin or a heparin peptide.

15. The method of claim 11 wherein the agent is orally administered in a series of doses effective to inhibit vascular smooth muscle cell proliferation associated with the procedure.

16. The method of claim 1 or 11 wherein the agent increases the cleavage of the latent form of TGF-beta.

17. The method of claim 1 or 11 wherein the agent increases the bioavailability of TGF-beta.

18. The therapeutic method of claim 1 or 11 wherein the agent is administered before, during, or after said procedure.

* * * * *

UNITED STATES PATENT AND TRADEMARK OFFICE
CERTIFICATE OF CORRECTION

PATENT NO. : 5,599,844

DATED : February 4, 1997

INVENTOR(S) : David J. Grainger et al.

It is certified that error appears in the above-identified patent and that said Letters Patent is hereby corrected as shown below:

In Claim 9, Column 15, line 27, please delete "2-[4-1,2-diphenyl-1-butenyl)" and insert --2-[4-(1,2-diphenyl-1-butenyl)--.

Signed and Sealed this

Fourteenth Day of October, 1997

*Attest:*

BRUCE LEHMAN

*Attesting Officer*   *Commissioner of Patents and Trademarks*